(12) United States Patent
Gunn et al.

(10) Patent No.: US 10,743,984 B2
(45) Date of Patent: Aug. 18, 2020

(54) OPTIC NERVE SUPPORT IMPLANT

(71) Applicant: Alcon Inc., Fribourg (CH)

(72) Inventors: Nicholas Max Gunn, Newport Beach, CA (US); Andrew David Johnson, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 102 days.

(21) Appl. No.: 15/928,311

(22) Filed: Mar. 22, 2018

(65) Prior Publication Data

US 2018/0271643 A1 Sep. 27, 2018

Related U.S. Application Data

(60) Provisional application No. 62/475,998, filed on Mar. 24, 2017.

(51) Int. Cl.
*A61F 2/14* (2006.01)
*A61L 31/14* (2006.01)
*A61L 31/04* (2006.01)
*A61L 31/06* (2006.01)
*A61F 9/00* (2006.01)
*A61F 9/007* (2006.01)
*A61L 31/02* (2006.01)
*A61F 2/00* (2006.01)

(52) U.S. Cl.
CPC .............. *A61F 2/14* (2013.01); *A61F 9/0017* (2013.01); *A61F 9/00781* (2013.01); *A61L 31/022* (2013.01); *A61L 31/04* (2013.01); *A61L 31/046* (2013.01); *A61L 31/048* (2013.01); *A61L 31/06* (2013.01); *A61L 31/145* (2013.01); *A61L 31/148* (2013.01); *A61F 2002/0081* (2013.01); *A61F 2210/0004* (2013.01); *A61F 2220/005* (2013.01); *A61F 2220/0008* (2013.01); *A61F 2230/0006* (2013.01); *A61L 2430/16* (2013.01); *A61L 2430/32* (2013.01)

(58) Field of Classification Search
CPC ...... A61F 2/14; A61F 9/0017; A61F 9/00781; A61F 2002/0081; A61F 2210/0004; A61F 2220/0008; A61F 2230/0006; A61L 31/022; A61L 31/04; A61L 31/046; A61L 31/06; A61L 31/145; A61L 31/148; A61L 2430/16; A61L 2430/32
See application file for complete search history.

(56) References Cited

U.S. PATENT DOCUMENTS 6,886,565 B2 * 5/2005 Morris ...................... A61F 9/04
128/846

* cited by examiner

*Primary Examiner* — David H Willse
*Assistant Examiner* — Tiffany P Shipmon

(57) ABSTRACT

Ophthalmic implants and methods of use that provide structural support to the optic nerve are disclosed herein. An adhesive and/or ophthalmic implant may be delivered to an optic nerve of an eye to relieve pressure on the optic nerve. The ophthalmic implant may include a base portion that includes a first surface and a second surface opposing the second surface and a protrusion from the second surface for extending into a cup of an optic nerve in an eye.

13 Claims, 5 Drawing Sheets

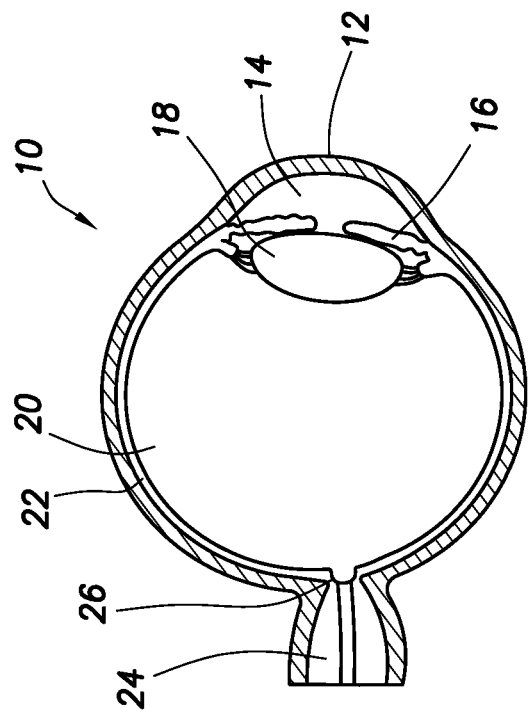
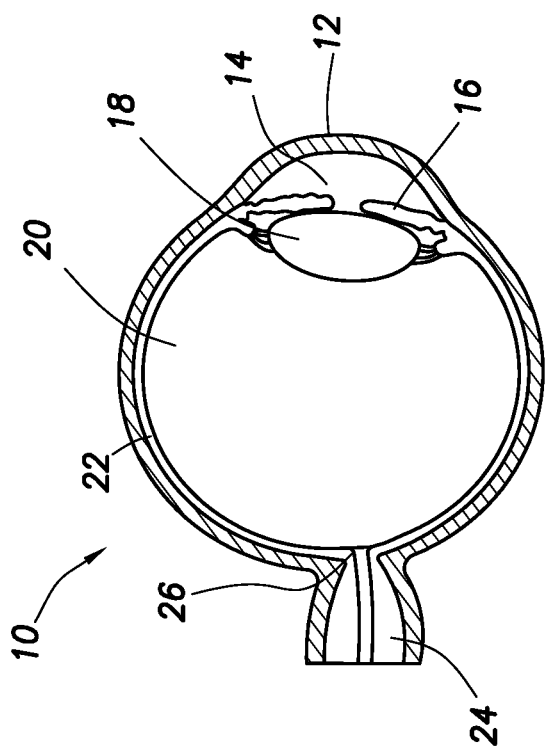

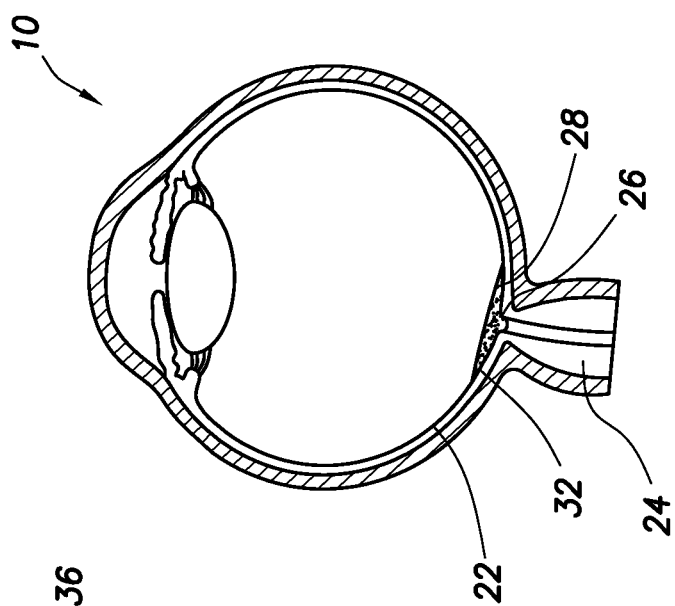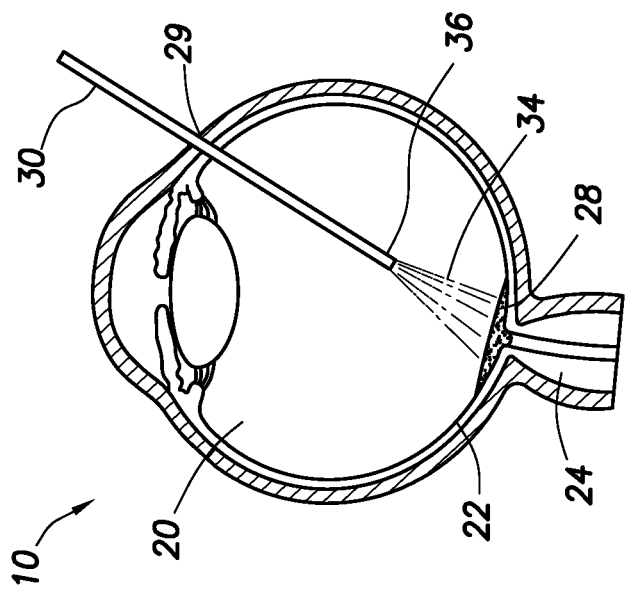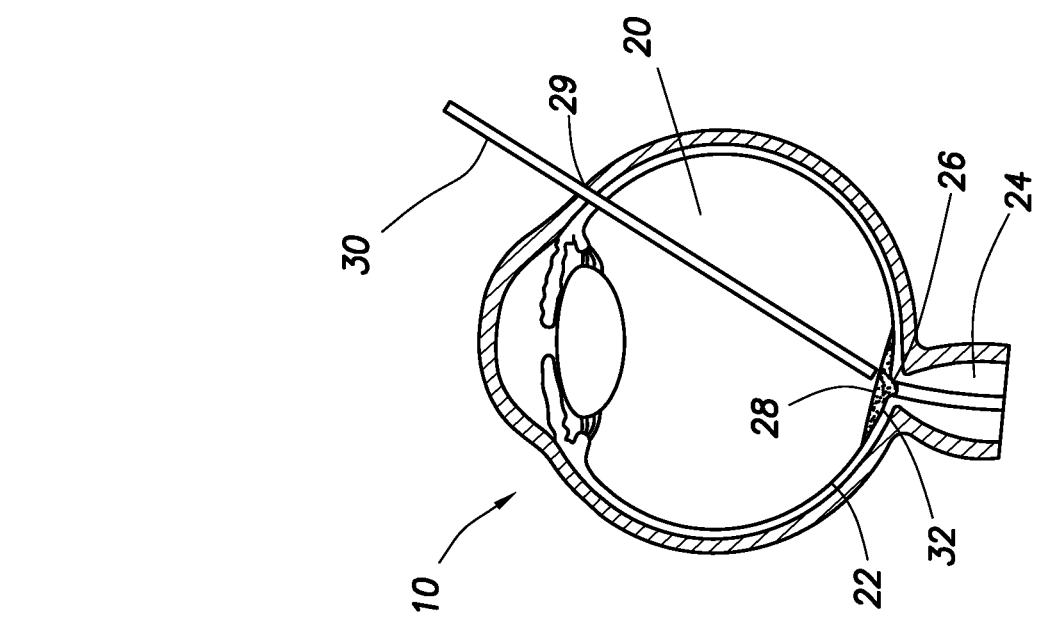

OPTIC NERVE SUPPORT IMPLANT

PRIORITY CLAIM

This application claims the benefit of priority of U.S. Provisional Patent Application Ser. No. 62/475,998 titled "OPTIC NERVE SUPPORT IMPLANT", filed on Mar. 24, 2017, whose inventors are Nicholas Max Gunn and Andrew David Johnson, which is hereby incorporated by reference in its entirety as though fully and completely set forth herein.

BACKGROUND

The eye is a specialized sensory organ capable of light reception and able to receive visual images. In the eye, the trabecular meshwork may serve as a drainage channel and may be located in the anterior chamber angle formed between the iris and the cornea. The trabecular meshwork may maintain a balanced pressure in the anterior chamber of the eye by allowing aqueous humor to flow from the anterior chamber. The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's intraocular pressure ("IOP").

Glaucoma is a group of eye diseases encompassing a broad spectrum of clinical presentations, etiologies, and treatment modalities. Glaucoma may cause pathological changes in the optic nerve, visible on the optic disk, and it may cause corresponding visual field loss, resulting in blindness if untreated. Most forms of glaucoma result when the IOP increases to pressures above normal for prolonged periods of time. The IOP can increase due to high resistance to the drainage of the aqueous humor relative to its production. Left untreated, an elevated intraocular pressure causes irreversible damage to the optic nerve and retinal fibers resulting in a progressive, permanent loss of vision.

Current therapies for glaucoma may be directed at decreasing intraocular pressure. Medical therapy may include topical ophthalmic drops or oral medications that may reduce the production or increase the outflow of aqueous humor. However, these drug therapies for glaucoma may be associated with side effects, such as, for example, headache, blurred vision, allergic reactions, death from cardiopulmonary complications, and potential interactions with other drugs. Additionally, even at reduced pressure, glaucoma patients may be susceptible to optic nerve damage and vision loss. Normal tension glaucoma may be characterized by damage to the optic nerve without an increase in IOP above physiologically normal levels. Because dropping IOP below physiological conditions may present a risk of hypotony, treatment of normal tension glaucoma may be limited.

SUMMARY

In an exemplary aspect, the present disclosure is directed to an ophthalmic implant. The ophthalmic implant may include a base portion that may include a first surface and a second surface opposing the second surface and a protrusion from the second surface for extending into a cup of an optic nerve in an eye.

In another exemplary aspect, the present disclosure is directed to a system for optic nerve support. The system may include an ophthalmic implant for attachment to an optic nerve of an eye and an adhesive for binding the ophthalmic implant to the optic nerve.

In another exemplary aspect, the present disclosure is directed to a method for providing support to an optic nerve. The method may include delivering an adhesive and/or ophthalmic implant to an optic nerve of an eye and adhering the adhesive and/or ophthalmic implant to the optic nerve, thereby providing structural support to the optic nerve.

The different aspects may include one or more of the following features. The base portion may be disc shaped. The protrusion may be located in a center of the second surface. A diameter of the protrusion may be about 1 millimeter (mm) to about 4 mm, and wherein a thickness of the ophthalmic implant at the protrusion may be about 1 mm to about 2 mm. The protrusion may be Gaussian or bell shaped. In some embodiments, the ophthalmic implant may include one or more protrusions. In some embodiments, the ophthalmic implant may not include a protrusion (e.g., the ophthalmic implant may be flat on both sides). The ophthalmic implant may be adapted to a shape of the optic nerve. The ophthalmic implant may have a diameter of about 2 mm to about 6 mm, and wherein the ophthalmic implant may have a thickness at a circumference of the base portion of about 0.25 mm to about 1 mm. The ophthalmic implant may include at least one material selected from the group consisting of polymethylmethacrylate, acrylic, silicone, and combinations thereof.

The different aspects may include one or more of the following features. The ophthalmic implant may include a base portion and a protrusion from the base portion for extending into a cup of the optic nerve. The protrusion may be located in a center of the base portion. A diameter of the protrusion may be about 1 mm to about 4 mm, and wherein a thickness of the ophthalmic implant at the protrusion may be about 1 mm to about 2 mm, wherein the ophthalmic implant may have a diameter of about 2 mm to about 6 mm, and wherein the ophthalmic implant may have a thickness at a circumference of the base portion of about 0.25 mm to about 1 mm. Other dimensions are also possible. For example, the dimensions of the ophthalmic implant may be adjusted according to the size of the eye (e.g., smaller for pediatric eyes). The protrusion may be Gaussian or bell shaped. The base portion may be disc shaped. Other shapes of the base portion and protrusion are also possible. For example, the shapes of the base portion and protrusion may be adjusted to fit the particular contours of a specific patient's eyes (e.g., as determined before/during the surgery). The ophthalmic implant may include at least one material selected from the group consisting of polymethylmethacrylate, acrylic, silicone, titanium, styrene isoprene butadiene, and combinations thereof. Other materials are also possible. The adhesive may include at least one adhesive selected from the group consisting of a hydrogel, an acrylic-based adhesive, a fibrin glue, and combinations thereof. Other adhesives are also possible. The adhesive may be curable with light (or, for example, heat).

The different aspects may include one or more of the following features. The ophthalmic implant may be adhered to the optic nerve with an adhesive. The ophthalmic implant may include a base portion and a protrusion from the base portion for extending into a cup of the optic nerve. The ophthalmic implant may include an adhesive, wherein the adhering the ophthalmic implant to the optic nerve may include curing the adhesive. In some embodiments, the adhesive may be permanent. In some embodiments, the adhesive (and, for example, the ophthalmic implant) may be made of materials that dissolve or absorb into the eye after a period of time.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

These drawings illustrate certain aspects of some of the embodiments of the present disclosure and should not be used to limit or define the disclosure.

FIG. 1A illustrates an example of a healthy eye where the optic nerve is healthy.

FIG. 1B illustrates an example of an eye with glaucoma where the optic nerve is damaged.

FIG. 2A illustrates an example of dispensing an adhesive into an eye.

FIG. 2B illustrates an example of curing an adhesive in an eye with light.

FIG. 2C illustrates an example of an eye with a cured adhesive attached to the optic nerve.

DETAILED DESCRIPTION

Figure 3A:
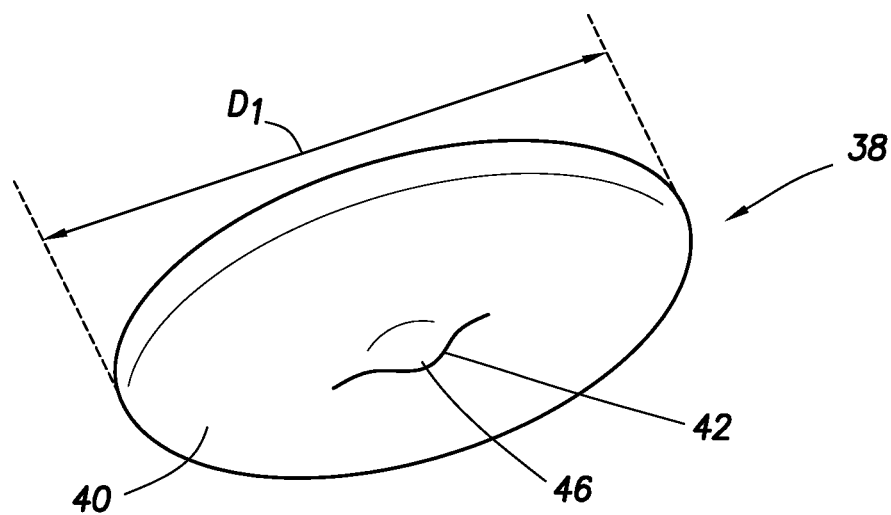
FIG. 3A illustrates an example of an ophthalmic implant.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure generally relates to treatment of the optic nerve, and, more particularly, to ophthalmic implants and methods of use that provide structural support to the optic nerve. By providing support to the optic nerve, example embodiments can limit or prevent optic nerve cupping and resultant problems. By way of example, supporting the optic nerve and, thus, preventing strain to the axons passing through the optic nerve, may reduce damage to nerve fibers that would ordinarily lead to vision loss. Example embodiments may be used to decrease potential damage to the optic nerve caused by glaucoma, regardless of the pressure being applied or the condition of the tissue within the eye. Accordingly, example embodiments may be used in the treatment of normal tension glaucoma where IOP may not be above physiologically normal levels. Additionally, example embodiments may stop vision loss rather than slow the progression of the vision loss as with pressure regulating methods.

FIGS. 1A and 1B schematically illustrate various portions of an eye 10. The eye 10 may include a cornea 12, anterior chamber 14, iris 16, lens 18, vitreous chamber 20, retina 22, and optic nerve 24. The anterior chamber 14 is disposed between the cornea 12 and the iris 16. The anterior chamber 14 may include aqueous humor. The vitreous chamber 20 is disposed between the lens 18 and the optic nerve 24. The vitreous chamber 20 may include vitreous humor. The optic nerve 24 may include a cup 26 in the center portion at the vitreous chamber 20. The cup 26 (or optic disc) may be visible as a crater-like depression. Glaucoma may cause the cup 26 to grow bigger as nerves are damaged. With specific reference to FIG. 1A, the eye 10 may be generally considered healthy with the cup 26 being relatively small. In contrast, the eye 10 shown in FIG. 1B is damaged by glaucoma with cup 26 being relatively large as compared to the cup 26 on FIG. 1A.

In accordance with example embodiments described herein, structural support may be provided within the eye 10 by an ophthalmic implant. Non-limiting examples of ophthalmic implants may include an adhesive (e.g., first adhesive 28 on FIGS. 2A-2C) and an implantable device (e.g., implantable device 38 on FIGS. 3A-3B). The ophthalmic implant may be relatively rigid in comparison with tissue of the optic nerve 24 to provide structural support, thus minimizing and potentially even preventing cupping. In some embodiments, the ophthalmic implant may be optically transparent. In some embodiments, the ophthalmic implant may be opaque. In some embodiments, the ophthalmic implant may include an additive to affect transmission of light through the implant. For example, the ophthalmic implant may include an additive to block ultraviolet light. Other additives are also possible (depending on the nature of light to be blocked). In some embodiments, the ophthalmic implant may be permanent. In other embodiments, the ophthalmic implant may be made of a material that slowly absorbs or dissolves in the eye. For example, the ophthalmic implant may be made of a material that absorbs into the eye within a range of 1 day to 1 month, 1 month to 6 months, 1 month to 1 year, 1 year to 2 years, 1 year to 5 years, 5 years to 10 years, 10 years to 25 years, etc. Other ranges of time are also possible. In some embodiments, the ophthalmic implant may include or may be coated with a drug to be slowly released into the eye. In some embodiments, the ophthalmic implant may be attached to the optic nerve 24 and the retina 22 surrounding the optic nerve 24. In some embodiments, the ophthalmic implant may not be attached to the optic nerve 24 and retina 22, but may instead overlay the optic nerve 24/retina 22 (without being attached). The ophthalmic implant may be implanted in the eye 10 following a vitrectomy. In some embodiments, the ophthalmic implant may be placed in the eye 10 without performing a vitrectomy.

FIGS. 2A-2C illustrate use of an implant in the form of the first adhesive 28. The first adhesive 28 may be any suitable curable adhesive for providing structural support to the optic nerve 24. The first adhesive 28 may include, for example, a hydrogel, an acrylic-based adhesive, a fibrin glue or combinations thereof. Suitable hydrogels may be injected into the eye or formed in the eye 10 by precursors having functional groups that form covalent crosslinks. Non-limiting of suitable hydrogels may include hydrogels based on polyether precursors for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly(vinyl pyrrolidinone) (PVP), poly (amino acids, dextran, or a protein). Additional examples of suitable hydrogels may include hydrogels based on gelatin methacryloyl ("GelMA") precursors. Suitable acrylic-based adhesives may include acrylic resins, for example, cyanoacrylates such as methyl-2-cyanoacrylate, ethyl-2-cyanoacrylate, n-butyl cyanoacrylate, and 2-octyl cyanoacrylate. Suitable fibrin glues may include two-component glues that include a first component including fibrinogen and a second component including thrombin. Any of a variety of different curing processes may be used to cure the first adhesive 28. For example, the first adhesive 28 may be cured by exposure to light (e.g., ultraviolet), heat, or a chemical curing agent, thereby hardening the first adhesive 28 securing the first adhesive 28 to the optic nerve 24. In some embodiments, the first adhesive 28 may not attach directly to the optic nerve 24, but may overlay the optic nerve 24 without attaching.

FIG. 2A illustrates placement of the first adhesive 28 into the eye 10 in accordance with example embodiments. An incision 29 may be made in the eye 10 to provide access to the vitreous chamber 20. Dispensing device 30 may be inserted through the incision 28 and into the vitreous chamber 20. The dispensing device 30 may include, but is not limited to, a cannula or other suitable surgical instrument that can be used to administer the first adhesive 28 into the eye 10. In some embodiments, the first adhesive 28 may be introduced through the dispensing device 30 and onto the optic nerve 24. In some embodiments, the first adhesive 28 may be introduced onto the optic nerve 24 and the retina 22. In some embodiments, the first adhesive 28 may completely cover the front surface 32 of the optic nerve exposed to the vitreous chamber 20, including the cup 26. As illustrated, the first adhesive 28 may fill the cup 26 formed in the optic nerve 24. The spatial extent of the placed/positioned first adhesive 28 may include portions of the optic nerve 24 other than the cup 26, in order to increase support/strength of the first adhesive 28. For example, the spatial extent of the dispensed first adhesive 28 may span past the typical cupping region of the optic nerve 24 for counter support of the ophthalmic implant.

FIG. 2B illustrates curing of the first adhesive 28 in accordance with example embodiments. As previously mentioned, any suitable curing process may be used for curing the adhesive, including, but not limited to, light, heat, or a chemical curing agent. In the illustrated embodiment, the first adhesive 28 may be exposed to light 34 for curing. The light 34 may be emitted from dispensing device 30. Dispensing device 30 may include a light source 36. The light source 36 for emitting the light 34 may include, for example, halogen bulbs, argon lasers and/or xenon arc lights. In some embodiments, curing times may be about 10 seconds to about 60 seconds. In other embodiments, curing times may be about 2 minutes to about 7 minutes. Other curing times are also possible. After curing, the dispensing device 30 may be removed from the eye 10.

FIG. 2C illustrates the adhesive after curing in accordance with example embodiments. As shown, the first adhesive 28 may cure (e.g., harden) to form an implant that is rigid and supports the optic nerve 24. In some embodiments, the first adhesive 28 may be attached to the optic nerve 24 as well as surrounding portions of the retina 22. In some embodiments, the first adhesive 28 may be attached to the cup 26 of the optic nerve 24. In other embodiments, the first adhesive 28 may be attached to the cup 26 and other portions of the front surface 32 of the optic nerve 24. The implant formed by the first adhesive 28 may have any suitable thickness, including, for example, a thickness ranging from about 0.25 millimeters ("mm") to about 2.0 mm.

Figure 3B:
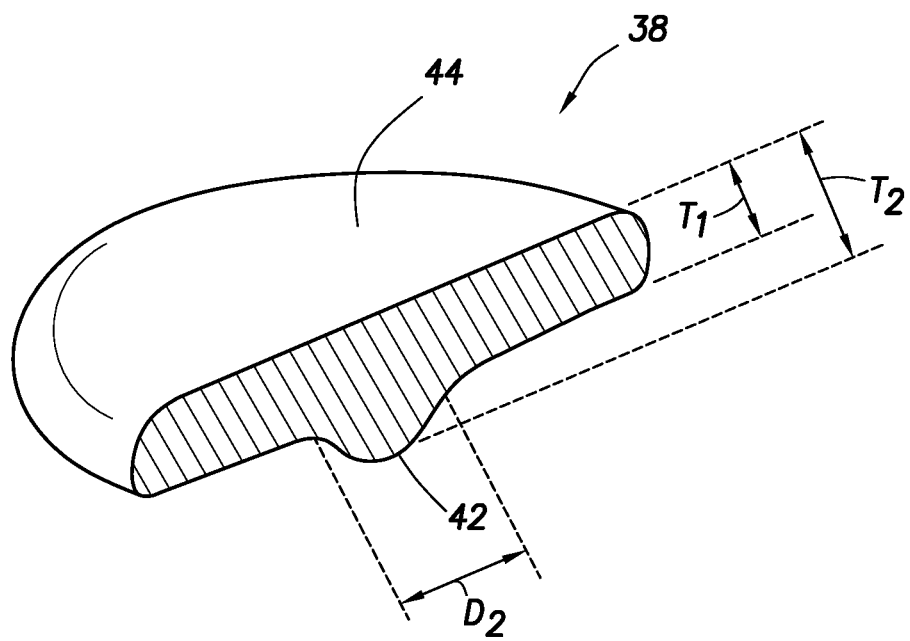
FIG. 3B illustrates a cross-sectional view of an example ophthalmic implant.

FIGS. 3A and 3B illustrate another embodiment of an implant for supporting the optic nerve 24 in the form of an implantable device 38. FIG. 3B is a cross-sectional view of the implantable device 38 of FIG. 3A. In some embodiments, the implantable device 38 may be adapted to the shape of optic nerve 24 without cupping. In some embodiments, the implantable device 38 may be rigid to support the optic nerve 24. The implantable device 38 may include a base portion 40 and a protrusion 42. In some embodiments, the base portion 40 may be axisymmetric (e.g., about the x-axis, about the y-axis, and/or about z-axis). The base portion 40 may have any suitable shape. Examples of suitable shapes for the base portion 40 may include, but are not limited to, cylindrical, disc-shaped, cubic, and hexahedral, among others. In some embodiments, the base portion 40 may have the general shape of an intraocular lens without haptics, for example.

Base portion 40 may include a first side 44 and a second side 46 opposing the first side 44. In the illustrated embodiment, the protrusion 42 extends from the second side 46. The protrusion 42 may be positioned on the second side 46 in any suitable position. In some embodiments, the protrusion 42 may be positioned on the second side 46 to fit into the cup 26 of the optic nerve 24 (e.g., shown on FIG. 1B) when implanted. As illustrated, the protrusion 42 may be positioned in the center of the second side, but may positioned in other suitable locations, depending, for example, on the particular configuration of the base portion 40. The protrusion 42 may be of any suitable shape, such as, for example, a Gaussian or bell shape. The surface of the protrusion 42 may correspond with the surface of optic nerve 24 (e.g., shown on FIG. 1B). In some embodiments, the ophthalmic implant may not include a protrusion (e.g., the ophthalmic implant may be flat on both sides).

The implantable device 38 may include any suitable material. Suitable materials may include, but are not limited to, polymethylmethacrylate ("PMMA"), acrylic, silicone, implantable metals (e.g., titanium), polymers (e.g., styrene isoprene butadiene) or combinations thereof. The implantable device 38 may have any suitable dimensions. Implantable device 38 may have a radius of curvature from about 10 mm to about 20 mm. In certain embodiments, a radius of curvature of implantable device 38 may be about 12 mm. In some embodiments, the base portion 40 may have a diameter $D_1$ from about 2 mm to about 6 mm. In a particular embodiment, the base portion 40 may have a diameter $D_1$ of about 4 mm. In some embodiments, the implantable device 38 may have a thickness $T_1$ from about 0.25 mm to about 1 mm at the circumference of the base portion 40, and a thickness $T_2$ from about 1 mm to about 2 mm at the protrusion 42. In a particular embodiment, the thickness $T_1$ of the implantable device 38 may be about 0.75 mm at the circumference of the base portion 40, and the thickness $T_2$ may be about 1.5 mm at the protrusion 42. In some embodiments, the protrusion 42 may have a diameter $D_2$ from about 1 mm to about 4 mm. In a particular embodiment, the protrusion 42 may have a diameter $D_2$ of about 1.9 mm. It should be understood that the particular dimensions given herein for the implantable device 38 are merely examples of some embodiments and the present embodiments should not be limited to these specific example dimensions. For example, dimensions outside these ranges may also be suitable for a particular application. Different eye dimensions may require different implantable device dimensions.

Figure 4:
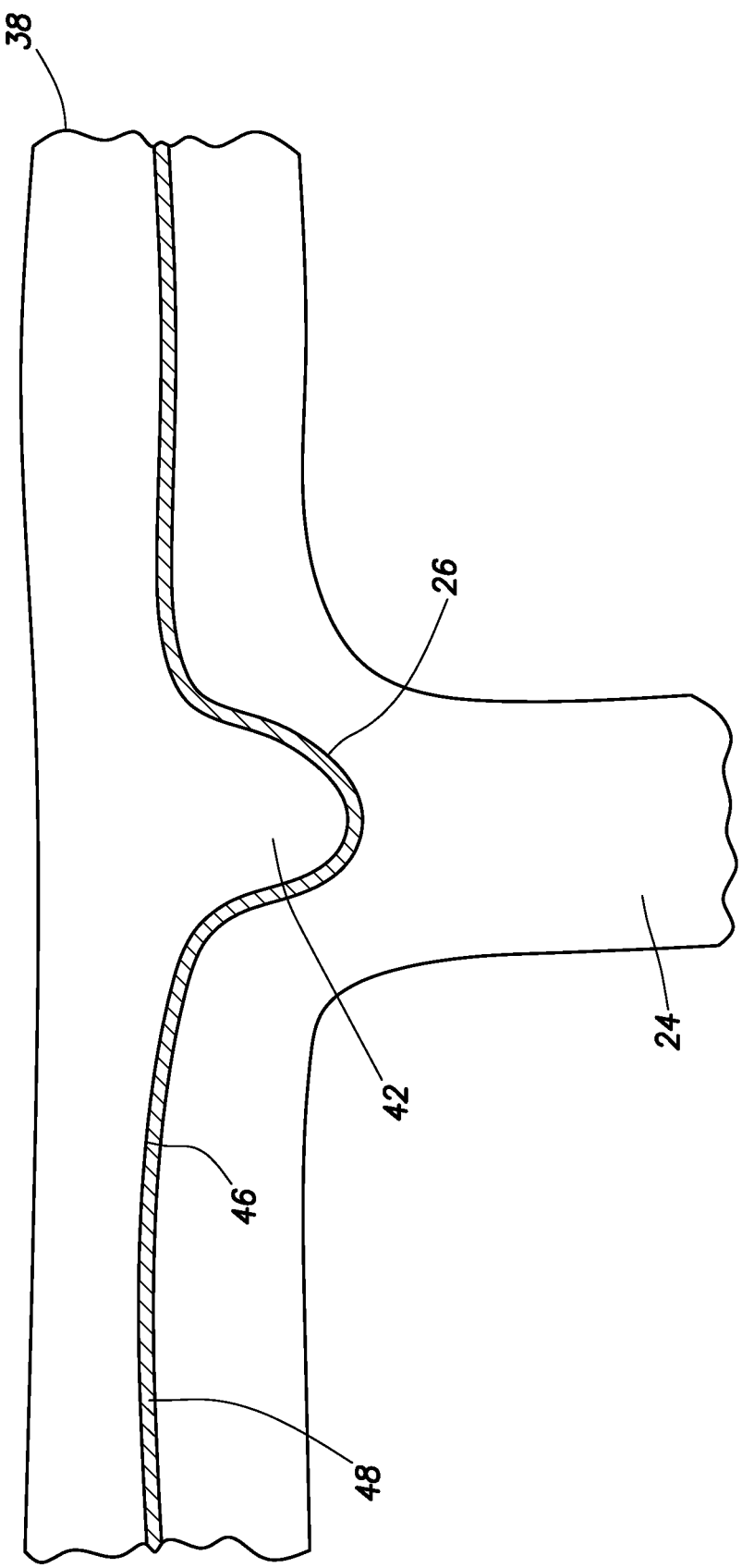
FIG. 4 illustrates a close-up view of an ophthalmic implant attached to the optic nerve of an eye.

FIG. 4 illustrates an example implantable device 38 disposed on optic nerve 24. In the illustrated embodiment, the second side 46 of the implantable device 38 is adjacent the optic nerve with protrusion 42 extending into the cup 26 of the optic nerve 24. In some embodiments, a second adhesive 48 secures the implantable device 38 to the optic nerve 24. As illustrated, the second adhesive 48 may be disposed between the implantable device 38 and the optic nerve 24. In some embodiments, the second adhesive 48 may the same type of curable adhesive as the first adhesive 28 described previously. In some embodiments, the second adhesive 48 may be a different type of curable adhesive than the first adhesive 28 described previously. The second adhesive 48 may be any suitable curable adhesive for securing the implantable device 38 to the optic nerve. The second adhesive 48 may include, for example, a hydrogel, an acrylic-based adhesive, a fibrin glue or combinations thereof. Any of a variety of different curing processes may be used to cure the second adhesive 48. For example, the second adhesive 48 may be cured by exposure to light (e.g., ultraviolet), heat, or a chemical curing agent, thereby hardening the second adhesive 48 securing the implantable device 38 to the optic nerve 24. In some embodiments, the second adhesive 48 may not secure the implantable device 38 to the optic nerve 24 (e.g., it may attach to different regions of the eye but still overlay the ophthalmic implant over the optic nerve 24). In some embodiments the pressure of the contents of the eye may press against the implantable device 38 to keep the implantable device 38 in place over the optic nerve 24.

Figure 5B:
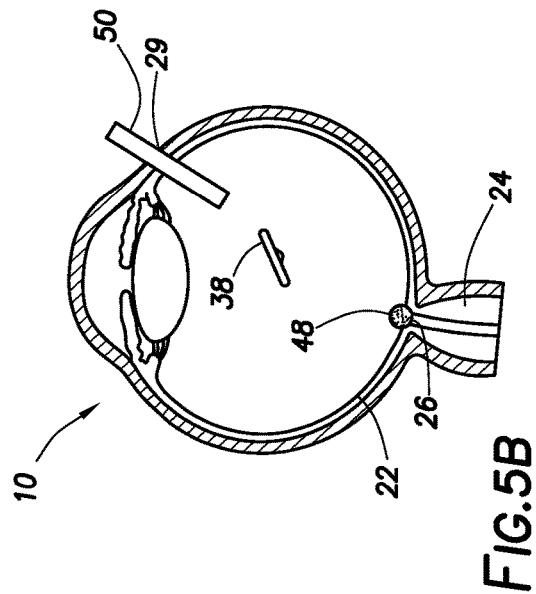
FIG. 5B illustrates an example of injecting an ophthalmic implant into an eye.
Figure 5D:
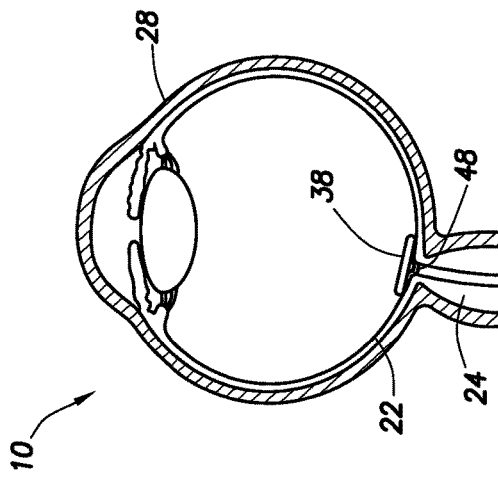
FIG. 5D illustrates an example of an eye with an ophthalmic implant attached to the optic nerve.
Figure 5A:
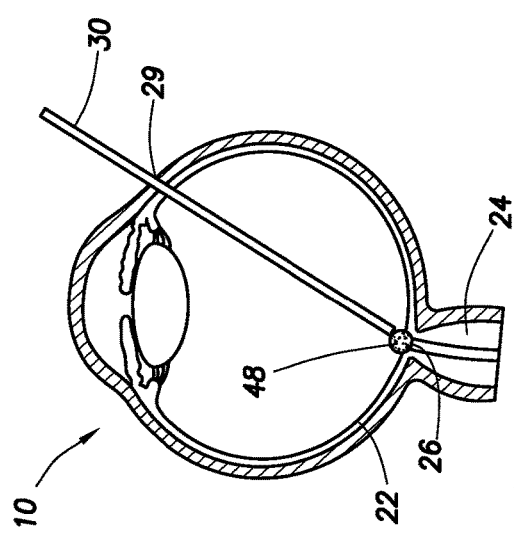
FIG. 5A illustrates an example of dispensing an adhesive into an eye.

Referring now to FIGS. 5A to 5D, use of the example implantable device 38 to support the optic nerve will now be described. FIG. 5A illustrates placement of the second adhesive 48 on the optic nerve 24 in accordance with example embodiments. An incision 29 may be made in the eye to provide access to the vitreous chamber 20. The dispensing device 30 may be inserted through the incision 29 and into the vitreous chamber 20. The dispensing device 30 may include a cannula or other suitable surgical instrument for delivery/administration of the second adhesive 48 into the eye 10. In some embodiments, the second adhesive 48 may be introduced through the dispensing device 30 and onto the optic nerve 24, including the cup 26. In some embodiments, the second adhesive 48 may also be introduced onto portions of the retina 22 surrounding the optic nerve 24. After placement of the second adhesive 48 against the optic nerve 24 and retina 22, the dispensing device 30 may be removed from eye 10 via incision 29. The first and second adhesives may be long term biocompatible adhesives. For example, the adhesives may hold for 1 day to 1 month, 1 month to 6 months, 1 month to 1 year, 1 year to 2 years, 1 year to 5 years, 5 years to 10 years, 10 years to 25 years, etc. Other ranges of time are also possible.

FIG. 5B illustrates placement of the example implantable device 38 into the eye 10 in accordance with example embodiments. In some embodiments, an implant injector 50 may be inserted through the incision 28 (or a different incision) and into the vitreous chamber 20. The implant injector 50 may include any suitable instrument for delivery of the implantable device 38 into the eye 30, such as, for example, an intraocular lens ("IOL") injector. In some embodiments, the implantable device 38 may be introduced into the vitreous chamber 20 by the implant injector 50. In some embodiments, the implant may be foldable or collapsible inside the implant injector 50 and may unfold or expand when exiting the implant injector 50 into the eye. In some embodiments, the implant injector 50 (or another device) may guide the implantable device 38 to the optic nerve 24. After placement of the implantable device 38, the implant injector 50 may be removed through the incision 29.

Figure 5C:
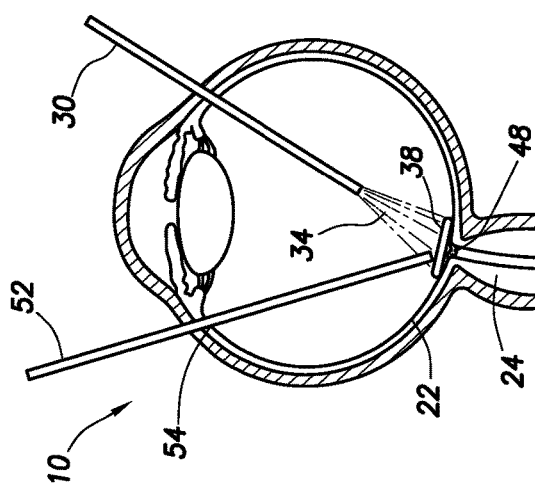
FIG. 5C illustrates an example of pressing and curing an ophthalmic implant to the optic nerve within an eye.

FIG. 5C illustrates securing of the example implantable device 38 to the optic nerve 24. As illustrated, the implantable device 38 may be positioned against the second adhesive 48. The second adhesive 48 may secure the implantable device 38 to the optic nerve 24. In some embodiments, the implantable device 38 may also be secured to the retina 22 (for example, to portions of the retina 22 surrounding the optic nerve 24). In some embodiments, a pressing instrument 52 may be inserted into eye 10 through a secondary incision 54. The pressing instrument 52 may hold the implantable device 38 against the second adhesive 48, for example, while curing. In some embodiments, the pressing instrument 52 may also be used to position the implantable device 38 against the second adhesive 48. The pressing instrument 52 may include, but is not limited to rods, vitreoretinal surgical instruments, such as, for example, a vitreous cutter, forceps, soft tip cannulas, illuminators, etc., or other suitable instruments for holding the implantable device 38 against the optic nerve 23. As previously mentioned, any suitable curing process may be used for curing the second adhesive 48, including, but not limited to, light, heat, or a chemical curing agent. In the illustrated embodiment, the second adhesive 48 may be exposed to light 34 for curing. The light 34 may be emitted from the dispensing device 30, which may include a light source 36. The light source 36 for emitting the light 34 may include, for example, halogen bulbs, argon lasers and/or xenon arc lights. In some embodiments, curing times may be about 10 seconds to about 60 seconds. In other embodiments, curing times may be about 2 minutes to about 7 minutes. Other curing times (based on the adhesive) are also possible. After curing, the dispensing device 30 may be removed from the eye 10.

FIG. 5D illustrates the example implantable device 38 secured to the optic nerve 24, in accordance with example embodiments. In the illustrated embodiment, the second adhesive 48 may secure the implantable device 38 to the optic nerve 24. In some embodiments, the second adhesive 48 may also secure the implantable device to portions of the retina 22 surrounding the optic nerve 24. As illustrated, the protrusion 42 of the implantable device 38 may extend into the cup 26 of the optic nerve 24. Accordingly, the implantable device 38 may provide structural support to the optic nerve 24, thus preventing (or reducing) vision loss due to cupping, for example.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:
1. An ophthalmic implant comprising:
a disc-shaped base portion comprising a first surface and a second surface opposing the first surface; and a centrally located protrusion from the second surface shaped and sized to extend into a cup of an optic nerve in an eye;

wherein the ophthalmic implant is optically transparent.

2. The ophthalmic implant of claim 1, wherein the centrally located protrusion is the only protrusion on the ophthalmic implant.

3. The ophthalmic implant of claim 1, wherein a diameter of the protrusion is about 1 mm to about 4 mm, and wherein a thickness of the ophthalmic implant at the protrusion is about 1 mm to about 2 mm.

4. The ophthalmic implant of claim 1, wherein the protrusion is Gaussian or bell shaped.

5. The ophthalmic implant of claim 1, wherein the ophthalmic implant comprises a biocompatible material that absorbs into the eye after 1 year.

6. The ophthalmic implant of claim 1, wherein the ophthalmic implant has a diameter of about 2 mm to about 6 mm, and wherein the ophthalmic implant has a thickness at a circumference of the base portion of about 0.25 mm to about 1 mm.

7. The ophthalmic implant of claim 1, wherein the ophthalmic implant comprises at least one material selected from the group consisting of polymethylmethacrylate, acrylic, silicone, and combinations thereof.

8. A system for optic nerve support comprising:
a disc-shaped ophthalmic implant shaped and sized to attach to an optic nerve of an eye, the ophthalmic implant comprising a base portion and a centrally located protrusion from the base portion shaped and sized to extend into a cup of the optic nerve, wherein the centrally located protrusion is the only protrusion on the ophthalmic implant, and further wherein a diameter of the protrusion is about 1 mm to about 4 mm, and wherein a thickness of the ophthalmic implant at the protrusion is about 1 mm to about 2 mm, wherein the ophthalmic implant has a diameter of about 2 mm to about 6 mm, and wherein the ophthalmic implant has a thickness at a circumference of the base portion of about 0.25 mm to about 1 mm; and an adhesive for binding the ophthalmic implant to the optic nerve.

9. The system claim 8, wherein the protrusion is Gaussian or bell shaped.

10. The system of claim 8, wherein the base portion is disc shaped.

11. The system of claim 8, wherein the ophthalmic implant comprises at least one material selected from the group consisting of polymethylmethacrylate, acrylic, silicone, titanium, styrene isoprene butadiene, and combinations thereof.

12. The system of claim 8, wherein the adhesive comprises at least one adhesive selected from the group consisting of a hydrogel, an acrylic-based adhesive, a fibrin glue, and combinations thereof.

13. The system of claim 8, wherein the adhesive is curable with light.

* * * * *